United States Patent
Carlucci et al.

(10) Patent No.: US 9,452,095 B2
(45) Date of Patent: Sep. 27, 2016

(54) ABSORBENT CORE HAVING IMPROVED STRUCTURE

(75) Inventors: Giovanni Carlucci, Chieti (IT); Alessandro Gagliardini, Villa Vomano (IT)

(73) Assignee: The Procter & Gamble Company, Cincinnati, OH (US)

( * ) Notice: Subject to any disclaimer, the term of this patent is extended or adjusted under 35 U.S.C. 154(b) by 1997 days.

(21) Appl. No.: 11/955,429

(22) Filed: Dec. 13, 2007

(65) Prior Publication Data

US 2008/0172017 A1   Jul. 17, 2008

(30) Foreign Application Priority Data

Jan. 12, 2007 (EP) .................... 07000630

(51) Int. Cl.
*A61F 13/537* (2006.01)
*A61F 13/535* (2006.01)
*A61F 13/15* (2006.01)
*A61F 13/53* (2006.01)

(52) U.S. Cl.
CPC ....... *A61F 13/535* (2013.01); *A61F 13/15203* (2013.01); *A61F 2013/15284* (2013.01); *A61F 2013/530547* (2013.01); *A61F 2013/530708* (2013.01)

(58) Field of Classification Search
CPC .......................................... A61F 2013/530766
See application file for complete search history.

(56) References Cited

U.S. PATENT DOCUMENTS

| | | | | |
|---|---|---|---|---|
| 4,260,443 A | * | 4/1981 | Lindsay et al. | 156/220 |
| 4,467,012 A | * | 8/1984 | Pedersen et al. | 442/118 |
| 4,537,590 A | * | 8/1985 | Pieniak et al. | 604/379 |
| 4,610,678 A | * | 9/1986 | Weisman et al. | 604/368 |
| 4,654,039 A | * | 3/1987 | Brandt et al. | 604/368 |
| 4,673,402 A | * | 6/1987 | Weisman et al. | 604/368 |
| 4,685,909 A | * | 8/1987 | Berg et al. | 604/360 |
| 4,988,344 A | * | 1/1991 | Reising et al. | 604/368 |
| 4,994,037 A | | 2/1991 | Bernardin | |
| 5,108,820 A | * | 4/1992 | Kaneko et al. | 428/198 |
| 5,217,445 A | * | 6/1993 | Young et al. | 604/381 |
| 5,262,223 A | | 11/1993 | Palumbo et al. | |
| 5,271,987 A | | 12/1993 | Iskra | |
| 5,300,054 A | * | 4/1994 | Feist | A61F 13/15203 604/358 |
| 5,364,382 A | * | 11/1994 | Latimer et al. | 604/378 |
| 5,494,940 A | * | 2/1996 | Unger et al. | 521/66 |
| 5,505,718 A | * | 4/1996 | Roe et al. | 604/368 |
| 5,509,914 A | * | 4/1996 | Osborn, III | 604/368 |
| 5,536,264 A | | 7/1996 | Hsueh et al. | |

(Continued)

FOREIGN PATENT DOCUMENTS

| | | |
|---|---|---|
| EP | 0 401 189 B2 | 6/1996 |
| EP | 1776967 A1 * | 4/2007 |
| WO | WO 2007047598 A1 * | 4/2007 |

OTHER PUBLICATIONS

European Search Report dated Jun. 15, 2007.

*Primary Examiner* — Paula L. Craig
(74) *Attorney, Agent, or Firm* — George H. Leal; Megan C. Hymore; David M. Weirich

(57) ABSTRACT

Absorbent core for disposable absorbent articles, particularly for the absorption of menses or blood. The absorbent core has at least two layers. A first layer having cellulose fibers that is substantially free of absorbent gelling materials; and a second layer having fibers and an absorbent gelling material and is substantially free of cellulose fibers.

17 Claims, 1 Drawing Sheet

(56) References Cited

U.S. PATENT DOCUMENTS

| | | | |
|---|---|---|---|
| 5,669,894 A | 9/1997 | Goldman et al. | |
| 5,681,300 A * | 10/1997 | Ahr et al. | 604/367 |
| 5,713,881 A | 2/1998 | Rezai et al. | |
| 5,741,241 A | 4/1998 | Guidotti et al. | |
| 5,843,058 A | 12/1998 | Quist | |
| 5,868,724 A | 2/1999 | Dierckes, Jr. et al. | |
| 5,913,850 A * | 6/1999 | D'Alessio et al. | 604/378 |
| 5,919,178 A | 7/1999 | Widlund | |
| 5,919,411 A | 7/1999 | Rezai et al. | |
| 5,925,299 A | 7/1999 | Dierckes, Jr. et al. | |
| 5,944,706 A | 8/1999 | Palumbo et al. | |
| 5,977,014 A | 11/1999 | Plischke et al. | |
| 6,068,620 A * | 5/2000 | Chmielewski | 604/378 |
| 6,232,250 B1 | 5/2001 | Palumbo et al. | |
| 6,372,952 B1 * | 4/2002 | Lash | A61F 13/4755 604/369 |
| 6,403,857 B1 | 6/2002 | Gross et al. | |
| 6,420,626 B1 * | 7/2002 | Erspamer | A61F 13/15617 428/131 |
| 6,610,902 B1 * | 8/2003 | Gustafsson et al. | 604/378 |
| 6,646,179 B1 | 11/2003 | Melius et al. | |
| 2002/0143308 A1 * | 10/2002 | Reeves et al. | 604/377 |
| 2002/0156411 A1 * | 10/2002 | Ahrens et al. | 602/54 |
| 2002/0165509 A1 * | 11/2002 | Baer et al. | 604/368 |
| 2003/0204178 A1 | 10/2003 | Febo et al. | |
| 2003/0219573 A1 * | 11/2003 | Falk | 428/195.1 |
| 2004/0247871 A1 | 12/2004 | Tsuchiya et al. | |
| 2005/0245684 A1 * | 11/2005 | Daniel et al. | 525/178 |
| 2006/0069367 A1 | 3/2006 | Waksmundzki et al. | |
| 2007/0027435 A1 * | 2/2007 | Nakagawa et al. | 604/368 |
| 2007/0093767 A1 * | 4/2007 | Carlucci et al. | 604/368 |
| 2007/0208315 A1 * | 9/2007 | Carlucci et al. | 604/378 |
| 2008/0091159 A1 * | 4/2008 | Carlucci et al. | 604/370 |

* cited by examiner

ABSORBENT CORE HAVING IMPROVED STRUCTURE

FIELD OF THE INVENTION

The present invention relates to an absorbent core for absorbent articles, for example sanitary napkins and the like.

BACKGROUND OF THE INVENTION

Absorbent articles for absorption of body fluids such as menses or blood are well known in the art, and comprise for example feminine hygiene articles such as sanitary napkins, panty liners, tampons, interlabial devices, as well as wound dressings, and the like. When considering for example sanitary napkins, these articles typically comprise a liquid-pervious topsheet as wearer-facing layer, a liquid-impervious backsheet as garment-facing layer and an absorbent core between topsheet and backsheet. The body fluids are acquired through the topsheet and subsequently stored in the absorbent core. The backsheet prevents the absorbed fluids from wetting the wearer's garment.

An absorbent core can comprise one or more fibrous absorbent material, which in turn can comprise natural fibers, such as for example cellulose fibers, typically wood pulp fibers, synthetic fibers, or combinations thereof, as known in the art, either as combination of different fibrous layers, e.g. batts or nonwovens or tissue layers, each constituted of a selected fiber type, or comprising layers made of different natural and/or synthetic fibers. Said structures can comprise different individual layers joined or combined together, or alternatively can be structures prepared by forming different layers in a continuous process, as will be defined in more detail further on.

It is also widely known in the art that it is beneficial for the absorption and retention characteristics of absorbent articles when portions of the article, typically the absorbent core, comprise superabsorbent materials, such as absorbent gelling materials (AGM), usually in finely dispersed form, e.g. typically in particulate form. Superabsorbent materials known in the art for use in absorbent articles typically comprise water-insoluble, water-swellable, hydrogel-forming crosslinked absorbent polymers which are capable of absorbing large quantities of liquids and of retaining such absorbed liquids under moderate pressure. Absorbent gelling materials can be incorporated in absorbent articles, typically in the core structure, in different known ways; for example, absorbent gelling materials in particulate form can be dispersed among the fibers of fibrous layers comprised in the core, or rather localized in a more concentrated arrangement between fibrous layers, or also in pockets, as it is known in the art.

In general, absorbent articles comprising absorbent gelling materials commonly have good absorption and retention characteristics to body fluids like urine; however, there still remains room for improvement of absorption and retention towards other body fluids. In particular, menses and blood are particularly difficult to be effectively absorbed and retained into absorbent articles containing superabsorbent materials since said materials do not show optimal absorption and retention characteristics towards said body fluids.

Such not optimal absorption and retention are mainly caused by poor permeability of superabsorbent materials towards menses and blood as such, in turn due to the viscosity and/or to the complex nature of these fluids. Menses and blood in fact are water based fluids comprising higher molecular weight and also corpuscular components, including red cells, white cells, soluble proteins, cellular debris and mucus, which slow down the absorption of these fluids by superabsorbents. Menses and blood are rather thick, hence inherently more difficult to absorb in conventional absorbent structures comprising absorbent gelling materials; moreover, corpuscular components like red cells may decrease the absorption capacity of certain superabsorbent particles. This translates into a slower initial uptake rate of the fluid into the superabsorbent material, and in turn in the absorbent structure comprising the superabsorbent material, which can result in a lower final absorption and retention capacity.

Also when considering more in general fibrous absorbent materials, it is known that different fibers and different fibrous structures as well, show different behaviors and effectiveness towards body fluids, particularly towards menses and blood. For example, cellulose fibers, such as for example wood pulp fibers, show a greater absorption and diffusion capacity towards the water fraction of menses and blood, which may be very rapidly acquired and may be transported within the fibrous structure, far from the initial acquisition area, while the corpuscular and higher molecular weight components do not diffuse equally well, and may remain closer to the initial acquisition area. Such corpuscular and higher molecular weight components tend to travel preferentially in a direction perpendicular to the plane of the absorbent structure. Also, natural and synthetic fibrous materials can be more or less suitable to provide compact, or alternatively bulkier, absorbent structures to be employed in absorbent cores.

The tendency, in the last years, has been towards thinner and more effective absorbent structures, taking advantage of the combination of typically fibrous structures with superabsorbent materials. Said thinner structures in turn provide absorbent articles combining a better comfort, discreetness and adaptability.

While a great deal of different absorbent core structures with various combinations and arrangements of fibers and absorbent gelling materials are known, there is still the need for an improved absorbent core structure for an absorbent article, particularly for absorption of menses or blood, which takes advantage of the peculiarities of the different absorbent materials in the absorption and management of these complex body fluids, achieving a better result in terms of fluid acquisition and distribution, in a structure which is stably thin, or in any case does not significantly change (for example increase) its thickness upon absorption throughout its normal use.

SUMMARY OF THE INVENTION

The present invention addresses the above need by providing an absorbent core for an absorbent article, which has a wearer facing surface and a garment facing surface; the core comprises a fibrous, layered structure of at least two layers, comprising:

a first layer which comprises cellulose fibers, and is substantially free of absorbent gelling materials, a second layer which comprises fibers and an absorbent gelling material, and is substantially free of cellulose fibers;

the core comprises less than 70% cellulose fibers; and the core comprises less than 70% absorbent gelling materials, wherein the percentages are percentages by weight, based on the dry weight of the core.

DETAILED DESCRIPTION OF THE INVENTION

The present invention relates to an absorbent core for absorbent articles such as sanitary napkins, panty liners, tampons, interlabial devices, wound dressings, and the like, which are intended for the absorption of body fluids, such as menses and blood. Exemplary absorbent articles in the context of the present invention are disposable absorbent articles. The term "disposable" is used herein to describe articles, which are not intended to be laundered or otherwise restored or reused as an article (i.e. they are intended to be discarded after a single use and preferably to be recycled, composted or otherwise disposed of in an environmentally compatible manner). The absorbent core of the present invention will be herein described in the context of a typical absorbent article, such as, for example, a sanitary napkin. Typically, such articles can comprise the elements of a liquid pervious topsheet, a backsheet and an absorbent core intermediate said topsheet and said backsheet.

In general, the topsheet should have good liquid transmission to maintain a dry surface and thereby keep the skin of the wearer dry. The absorbent core shall provide the desired absorbent capacity and can also allow the flow of vapor and/or air through it. The backsheet should generally prevent wet through to retain the absorbed fluid; the backsheet can also be breathable. Furthermore, the individual elements can be joined to each other such that the final product has the desired comfort and performance level.

In the following description the term "cellulose fibers" is used. Cellulose fibers comprise naturally occurring fibers based on cellulose, such as, for example cotton, linen, etc. Wood pulp fibers are one example of cellulose fibers according to the present invention. Man-made fibers derived from cellulose, such as regenerated cellulose (rayon), or partially or fully acetylated cellulose derivatives (e.g. cellulose acetate or triacetate), are also considered as cellulose fibers according to the present invention.

In the following description of the invention the surface facing in the direction of the wearer is called wearer-facing surface. Further, the surface facing in the direction of the garment is called a garment-facing surface. The absorbent article of the present invention, as well as any element thereof, such as, for example the absorbent core, has therefore a wearer-facing surface and a garment-facing surface.

Absorbent Article Components

Topsheet

Figure 1:
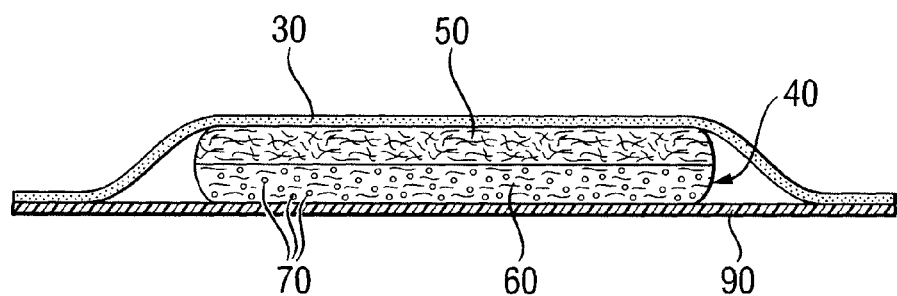
FIG. 1 is a schematic cross section of a sanitary napkin showing the internal layered structure of the absorbent core according to an embodiment of the present invention.

According to the present invention the absorbent article can comprise a liquid pervious topsheet. The topsheet suitable for use herein can comprise wovens, nonwovens, and/or three-dimensional webs of a liquid impermeable polymeric film comprising liquid permeable apertures. In FIG. 1 the topsheet is indicated with reference numeral 30. For example, the wearer-facing and contacting surface can be provided by a film material having apertures which are provided to facilitate liquid transport from the wearer facing surface towards the absorbent structure. Such liquid permeable, apertured films are well known in the art. They provide a resilient three-dimensional fiber-like structure. Such films have been disclosed in detail for example in U.S. Pat. No. 3,929,135, U.S. Pat. No. 4,151,240, U.S. Pat. No. 4,319,868, U.S. Pat. No. 4,324,426, U.S. Pat. No. 4,343,314, U.S. Pat. No. 4,591,523, U.S. Pat. No. 4,609,518, U.S. Pat. No. 4,629,643, U.S. Pat. No. 4,695,422 or WO 96/00548.

The topsheet for use herein can be a single layer or may have a multiplicity of layers. In an embodiment of the present invention, the topsheet across its full extension is a single layer, which provides both the wearer-facing surface and the garment-facing surface of the topsheet. Optionally, on the wearer-facing surface of the topsheet but only extending in the peripheral zone of the article an additional layer may be desirable to provide extra softness or extra liquid handling/retaining abilities (this design is usually referred to as "hybrid topsheet"). The topsheet typically extends across the whole of the absorbent structure and can extend into and form part of or all of the preferred but optional side flaps, side-wrapping elements, wings or ears. Also the topsheet can wrap around the absorbent core edges.

The topsheet as a whole shall be compliant, soft feeling, and non-irritating to the wearer's skin. It also can have elastic characteristics allowing it to be stretched in one or more directions. The topsheet may provide for acquisition and transport of fluid from the wearer towards the absorbent core and containment of the absorbent core. In addition to liquid permeability, the topsheet may have a high vapor permeability and/or air permeability.

Absorbent Core

According to the present invention, the absorbent core is a layered structure which may if desired be a structure, which despite potential internal variations of physical and/or chemical characteristics is provided such that it cannot be separated into individual layers. Such structures are well known in the art and can be prepared by forming the different layers in a continuous process, for example by air laying techniques. Structures made from a number of individual layers, which are combined or also joined to each other by e.g. macroscopic mechanical or adhesive means, can instead be separated from each other again, although sometimes with difficulty. Such structures can also alternatively constitute the absorbent core according to the present invention, wherein individual layers having the desired characteristics can be combined and possibly joined according to methods known in the art, for example by means of adhesive, or thermal, or mechanical bonding, or any combination thereof.

In certain embodiments, the absorbent core 40 of the present invention can have an overall calliper or thickness in the dry state of less than about 12 mm, or of less than about 8 mm, or of less than about 5 mm, or also from about 2 mm to about 0.5 mm. The basis weight of the absorbent core 40 can range from about 50 g/m$^2$ to about 300 g/m$^2$, or from about 90 g/m$^2$ to about 250 g/m$^2$, or also from about 100 g/m$^2$ to about 150 g/m$^2$. In the context of the present invention, calliper or thickness of structures or layers, either in dry or wet conditions, is meant to be measured with any suitable device which is known in the art, under a specified pressure. According to the present invention, said calliper or thickness is measured under a pressure of 20 g/cm$^2$ (1.96 kPa), for example with a calliper from Loerentzen & Wettre (Box 4 S-16393 Stockholm) APP 51D20 Type 02101, under the pressure as stated above and over an area of 10 cm$^2$.

The absorbent core 40 has a wearer facing-surface and a garment-facing surface, and according to the present invention comprises at least two layers: a first layer 50, which comprises cellulose fibers and is substantially free of absorbent gelling materials, and a second layer 60 adjacent to said first layer, which comprises fibers and an absorbent gelling material 70, and is substantially free of cellulose fibers. By saying that a layer of the absorbent core is "substantially free" of absorbent gelling material or of cellulose fibers, it is meant in the context of the present invention that the layer should not comprise any significant amount of the selected element within its inner structure. While cellulose fibers or absorbent gelling material which can be present at an outer surface of the specified layer, for example at the interface between the specified layer and an adjacent one, in some cases accidentally and slightly penetrating the structure of the specified layer, such shall not be considered significant. Significant amount can correspond to less than about 5% by weight, or to less than about 3% by weight, or also to less than about 1% by weight, based on the dry weight of the specified layer of the absorbent core.

According to an embodiment of the present invention, the first layer 50 can be on the wearer-facing surface of the absorbent core 40 and can actually constitute said wearer-facing surface as illustrated in FIG. 1, while the second layer 60 can be below the first layer and adjacent thereto on the garment-facing surface of the core, in certain embodiments constituting said garment-facing surface, as shown in the embodiment of FIG. 1.

According to the present invention, the absorbent core 40 overall comprises less than about 70% cellulose fibers, or less than about 55%, or also from about 10% to about 40%, and less than about 70% absorbent gelling materials, or from about 10% to about 40%, wherein all percentages are to be considered percentages by weight, based on the dry weight of the absorbent core 40.

It has been surprisingly discovered that an absorbent core having the above characteristics provides an improved absorption and handling capacity towards body fluids, particularly complex body fluids such as menses and blood, in a structure which is typically thin and comfortable, and with an improved dimensional stability, as will be explained in detail below.

The absorbent core is substantially thin and does not significantly change its calliper when passing from a dry condition to a wet condition, i.e., maintains its thickness upon liquid absorption close to the value shown in dry conditions. This dimensional stability can be expressed, in the context of the present invention, by comparison of the dry density with the wet density. Density of an absorbent structure, for example of an absorbent core according to the present invention, is expressed in $g/cm^3$ and, as known to the skilled man, can be straightforwardly calculated from the basis weight ($g/m^2$) and the calliper (mm) of a layer, by suitably adapting the units, wherein the calliper is evaluated both in dry and wet state as specified above, under a pressure of 20 $g/cm^2$ (1.96 kPa). The dry density, as well as any other parameter identified with the word "dry" e.g. the dry weight, is evaluated on the dry structure or layer, wherein by "dry structure or layer" it is meant a structure after a conditioning of 24 hours at 25° C. and 50% Relative Humidity. The wet density is evaluated after soaking a suitable sample of the structure in Artificial Menstrual Fluid (AMF) for 120 minutes until saturation is achieved, and subsequent elimination of any excess fluid by keeping the sample hanging for five minutes, or in any case until dripping substantially stops. The basis weight for the wet density is the basis weight of the sample saturated with AMF after elimination of any excess fluid as explained above. The AMF is prepared according to the method described below.

The absorbent core of the present invention is capable of absorbing relevant amounts of body fluids, such as for example menses or blood, by substantially increasing its density and without excessive increase of its thickness in wet conditions, despite it comprising relatively moderate percentages of cellulose fibers and of absorbent gelling materials. The absorbent core of the present invention hence has an increased efficiency in absorbing and handling complex body fluids such as typically menses and blood.

According to an embodiment of the present invention, the absorbent core has a wet density which can be from 5 to 20 times greater than the dry density, or from 8 to 15 times greater than the dry density, which implies the initially thin structure increases its density upon liquid absorption, thus keeping its thickness almost constant or only slightly increasing, without showing a significant swelling, which instead would make the absorbent core, and in turn the absorbent article comprising it, more cumbersome and possibly less comfortable during use. The absorbent core of the present invention hence employs more efficiently the absorbent capacity of its constituent materials.

The dry density of the absorbent core of the present invention can be between about 0.04 $g/cm^3$ and about 0.3 $g/cm^3$, or between about 0.08 $g/cm^3$ and about 0.15 $g/cm^3$.

First Layer

The first layer 50 is a fibrous layer comprising cellulose fibers and being substantially free of absorbent gelling materials. The cellulose fibers can consist, for example, of wood pulp fibers, but other cellulose fibers as explained above can be used, as an alternative to or in combination to wood pulp fibers. A small amount of synthetic fibers can also be included in the first layer 50, up to a percentage of about 20% by weight, or of about 15% by weight, or also between about 7% and about 12% by weight, based on the dry weight of the entire first layer 50. Suitable synthetic fibers can be selected among those known in the art, for example bicomponent fibers, such as known polyethylene/polypropylene fibers, can be comprised in the first layer 50 in combination with the cellulose fibers. A latex can also be added to the fibers of the first layer 50, in percentages of less than about 10% by weight of the entire first layer 50, or from about 2% to about 5% by weight. Addition of latex can be used to improve the dimensional stability of the first layer 50, which is in turn relevant for the dimensional stability of the entire absorbent core. The presence of synthetic fibers, such as for example bicomponent fibers, followed by a suitable heat treatment as known in the art, can also provide dimensional stability to the first layer 50 in dry and wet conditions.

The first layer 50 can have an overall basis weight from about 20 $g/m^2$ to about 100 $g/m^2$, or from about 30 $g/m^2$ to about 60 $g/m^2$.

Second Layer

The second layer 60 comprises an absorbent gelling material 70 and is substantially free of cellulose fibers. Any kind of fibers which are known in the art, besides cellulose fibers, can be included in the second layer 60. Known synthetic fibers such as, for example, polyethylene, polypropylene, polyester, polyamide fibers can be used. Bicomponent fibers can also be used in the second layer 60.

As used herein the term bicomponent fibers refers to fibers having two constituents. Typically bicomponent fibers are constituted of relatively similar constituents, which are differing, for example in their melting temperature or softening temperature. Particular embodiments in the context of the present invention are polypropylene/polyethylene bicomponent fibers but other combinations such as polyester/polyethylene, polyester/polypropylene, polyamide/polyester, polyamide/polyethylene, and polyamide/polypropylene are also feasible combinations. The conventionally used material can be, however, the above-mentioned polypropylene/polyethylene fiber composition which is provided in a form such that in a cross-sectional view of a fiber the material with the higher melting or softening point provides the central part or the core of the fiber and typically is responsible for the fiber ability to transmit forces and have a certain rigidity or provide structures with resiliency while the outer coating on the core of the fiber has a lower melting point and is used to facilitate thermal bonding of substrates comprising such fibers. The so-called shaft core design of bicomponent fibers can be not exactly point-symmetrical to the central point of the cross section but provides the shaft part of the fiber in an asymmetric form so that the fiber is caused to curl. This has been found to provide a beneficial effect on resiliency and strength of the fiber.

In a typical embodiment according to the present invention, a polypropylene core is provided with a polyethylene coating on the outside in an asymmetric form such that about 50% of the fiber material is polypropylene and about 50% of the fiber material is polyethylene. Other quantitative amounts can of course be selected and will strongly depend on the overall fiber dimensions as the binder quantity of the surface of the fiber provided preferably by the polyethylene needs to have a certain thickness in absolute terms for the provision of good bonding while its relative quantity can vary.

The second layer 60 comprises also one or more absorbent gelling material 70. The absorbent gelling materials are capable of absorbing large quantities of aqueous body fluids, and are further capable of retaining such absorbed fluids under moderate pressures. The absorbent gelling materials can be dispersed homogeneously or non-homogeneously within the structure of the second layer 60, namely among the fibers.

According to the present invention, suitable absorbent gelling materials for use herein can be selected among polyacrylate based materials, typically in particle form. The polyacrylate based materials incorporated in the absorbent articles of the present invention are polyelectrolytes with a multiplicity of anionic functional groups, typically carboxyl groups. In certain embodiments, the polyacrylate based materials can comprise polyacrylates, polymethacrylates, and derivatives thereof, such as for example polyacrylate sodium, polymethacrylate sodium, polyacrylate potassium, polymethacrylate potassium, starch grafted polyacrylate, starch grafted polymethacrylate, polyvinyl alcohol grafted polyacrylate, polyvinyl alcohol grafted polymethacrylate, cellulose grafted polyacrylate, cellulose grafted polymethacrylate, and the like. In an embodiment of the present invention, the absorbent gelling material can be a crosslinked, partially neutralized polyacrylate.

The polyelectrolytes which provide the polyacrylate based materials incorporated in the absorbent articles of the present invention can be made from polymerizable, unsaturated, acid-containing monomers. Such monomers include the olefinically unsaturated acids and anhydrides which contain at least one carbon to carbon olefinic double bond. More specifically, these monomers can be selected from olefinically unsaturated carboxylic acids and acid anhydrides, olefinically unsaturated sulfonic acids, and mixtures thereof.

Polyacrylate based materials, typically partially neutralized polymers, are commonly incorporated in absorbent articles and are known as superabsorbent polymers (SAP), or superabsorbents, and are crosslinked. The polyacrylate material has neutralized, typically with sodium, carboxylate groups hanging off the main polymer chain. In contact with water, the sodium detaches and goes in solution, leaving only carboxyl ions. Being negatively charged, these ions repel one another so that the polymer unwinds and absorbs more and more water, which is instead attracted by the carboxyl ions, as further carboxyl ions become available. The hydrogen in water is trapped by the polyacrylate due to the atomic bonds associated with the polarity forces between the atoms. The cross-links, which bridge different polymer chains, lead to a three dimensional structure, which upon liquid absorption constitutes the swollen gel.

According to an embodiment of the present invention, the absorbent gelling material which can be comprised in the second layer 60 of the absorbent core can be selected among the polyacrylate based polymers described in the European Patent Application EP 05023061.4, filed on 21 Oct. 2005 in the name of The Procter and Gamble Company. As explained in the referenced application, polyacrylate based materials being very slightly crosslinked, or substantially not crosslinked at all, incorporated in absorbent articles for the absorption of proteinaceous or serous body fluids such as for example menses, blood, plasma, vaginal secretions, and also mucus or milk, but particularly menses or blood, provide an improved absorption and retention capacity for such body fluids, and an improved absorption rate as well, compared to traditional crosslinked superabsorbents.

According to the above referenced application, a measure of the degree of crosslinking of a polyacrylate based polymer can be expressed in terms of the soluble or extractable fraction of the polymer. As it is known in the art, lower molecular weight polymer chains can be solubilized, or extracted, from the polymer in certain conditions, and represent said soluble or extractable fraction of the polymer itself. Generally, the extractable fraction can be considered to be inversely proportional to the degree of crosslinking, that is, the higher the degree of crosslinking, the lower the fraction, since a greater proportion of the polymer mass is actually incorporated into the polymer network. Such polyacrylate based polymer which can be incorporated in an absorbent article for absorption of proteinaceous or serous body fluids, particularly menses, has an extractable fraction of more than about 15%, or of more than about 20%, or of more than about 30% by weight. Desirably, said extractable fraction can be not more than about 60% by weight of the polyacrylate based material, or not more than about 50% by weight. The extractable fraction is evaluated according to the Extractables Test described in the above referenced European Patent Application EP 05023061.4.

The absorbent gelling materials can be typically used in the form of discrete particles. Such absorbent gelling materials can be of any desired shape, e.g., spherical or semi-spherical, cubic, rod-like polyhedral, etc. Shapes having a large greatest dimension/smallest dimension ratio, like needles and flakes, are also contemplated for use herein. Agglomerates of absorbent gelling material particles may also be used.

The size of the absorbent gelling material particles may vary over a wide range. For example, particle sizes between about 10µ and about 1,000µ, or between about 50µ and about 1,000µ, or between about 100µ and about 800µ, or between about 150µ and about 600µ can be used. "Particle Size" as used herein means the weighted average of the smallest dimension of the individual particles.

According to an embodiment of the present invention, the absorbent gelling material can be provided in the second layer 60 of the absorbent core 40 in a basis weight of about 2 g/m² to about 100 g/m², or of about 10 g/m² to about 90 g/m², or of about 20 g/m² to about 50 g/m², typically depending on the desired absorption capacity of the absorbent article comprising the core, as it is known in the art. The absorbent gelling material can constitute from about 10% to about 95% by weight, based on the dry weight of the second layer 60, or from about 50% to about 90%, or from about 70% to about 85%.

The second layer 60 can have an overall basis weight from 20 g/m² to 100 g/m², or also from 30 g/m² to 60 g/m².

According to the present invention, the second layer 60 also has an improved dimensional stability both in dry and wet state, i.e. without substantially increasing the calliper upon liquid absorption. This can be provided for example by an appropriate heat treatment of a second layer 60 comprising bicomponent fibers and particles of absorbent gelling material, as it is known in the art, which results in partial fusion of the outer coating of the bicomponent fibers, with creation of bonds. Other means known in the art can be used to provide the second layer 60 with dimensional stability can be for example the inclusion of fine adhesive fibers within the structure, or of thermofusible, heat activatable thermoplastic particles such as polyethylene powder.

Optional Third Layer

Figure 2:
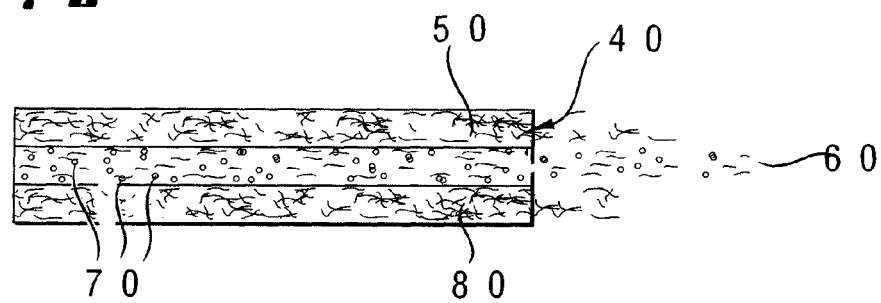
FIG. 2 is a schematic cross section of an absorbent core according to an alternative embodiment of the present invention.

According to an alternative embodiment illustrated in FIG. 2, the absorbent core 40 of the present invention can further comprise a third layer 80 adjacent to the second layer 60, which, in the embodiment of FIG. 2, can be on the garment facing surface, actually constituting said garment facing surface in a three layer structure. The third layer 80 can have substantially the same structure as the first layer 50, i.e. comprising cellulose fibers, and optionally synthetic fibers, and being substantially free of absorbent gelling materials. Materials and compositions of this optional third layer can be the same as specified above for the first layer of the absorbent core.

The optional third layer 60 can have an overall basis weight from about 20 g/m² to about 100 g/m², or from about 30 g/m² to about 60 g/m².

According to an embodiment of the present invention, the absorbent core can be provided as a single structure by known means. Thermo bonding or felting or combinations of these combining steps can for example create it. Hence, a core constituted by a single structure can be provided by laying the various materials described above onto each other in a continuous process, for example by air laying techniques, then a calendaring can take place in order to reduce the thickness and bulkiness of the structure as desired. The calendaring step can create a densification, which can provide the same force throughout the whole of the structure. This calendaring can be then optionally followed by thermo bonding or felting with needles or a combination such as felting with hot needles and a hot air exposure of the absorbent core structure, in order to attain a desired level of calliper, density and structure stabilization, which will in turn reflect on the final dimensional stabilization of the absorbent core.

Alternatively, the absorbent core of the present invention can also be provided by combining and optionally joining with known means different separately formed individual layers having the desired characteristics as explained above.

Without being bound to any theory, it is believed that the absorbent core of the present invention has an improved capacity for the acquisition, management and retention of complex body fluids, particularly menses and blood, owing to the particular combination and composition of its material components, and, in an embodiment of the present invention, also to the respective arrangement thereof.

In the absorbent core of the present invention, the at least first and second layer can each provide specific liquid absorption and management characteristics. Namely, the first layer comprising cellulose fibers and being substantially free of absorbent gelling materials provides a fast acquisition of the fluid, typically menses or blood, rapidly wicking and transporting the aqueous fraction and substantially transmitting the corpuscular and complex fraction through its thickness. As no superabsorbent material is present in the first layer, there is no risk its overall absorption capacity is impaired by poor absorption characteristics of absorbent gelling material towards the corpuscular and complex fraction of the body fluid, typically menses or blood. The second layer instead comprises synthetic fibers and superabsorbent material and is substantially free of cellulose fibers, wherein the synthetic fibers have a sort of filtration capacity towards the corpuscular and complex fraction of menses or blood, which is then intercepted minimizing its direct interaction with the superabsorbent material, which could otherwise cause gel blocking. The superabsorbent material in this arrangement is instead capable of better absorbing the fluid. This is achieved in a structure which is typically thin and is capable of employing more completely the absorption capacity of the different materials, which can hence be present in a typically lesser amount, thus also providing a particularly thin structure having improved dimensional stability during absorption and therefore increased comfort during use.

The absorbent core of the particular embodiment of the present invention specifically illustrated in FIG. 1 is capable of providing an even improved fluid management and absorption capability towards complex body fluids such as menses and blood, owing to the particular arrangement of its components. The absorbent core, typically enclosed in an absorbent article, receives the body fluid in its first layer which comprises cellulose fibers and is substantially free of absorbent gelling material. As known, cellulose fibers can absorb and transport water very efficiently, hence when a body fluid such as menses or blood having a water fraction and a more complex fraction comprising corpuscular components, including red cells and white cells, soluble proteins, cellular debris and mucus, is acquired by the first layer of the absorbent core of the present invention, the water fraction is readily transported both through the thickness of the layer, in what can be called the z-direction, i.e. perpendicular to the plane of the layer, and also wicked within the layer itself, far from the acquisition region, for capillarity, in what can be called the xy-plane, parallel to the plane of the layer. The complex fraction of menses or blood instead remains rather concentrated close to the acquisition region, and typically travels in z-direction, towards the underlying second layer.

The second layer in turn is substantially free of cellulose fibers and comprises instead typically synthetic fibers and absorbent gelling material distributed therein. The synthetic fibers have a sort of separating capacity towards the complex fraction menses or blood, particularly towards the corpuscular components like read and white cells, which are hence to a certain extent filtered or blocked, so as to limit their interference with the superabsorbent material dispersed within the fibrous structure of the second layer. As known, complex components of menses or blood, particularly corpuscular components, tend to accumulate on the outer surface of the absorbent gelling material, for example superabsorbent particles, with a sort of shielding effect which causes gel blocking and prevents further absorption.

This can be avoided in the absorbent core of the present invention, which instead takes advantage of the peculiar and also contrasting characteristics of the different materials thereof, at an even greater extent in the specific arrangement of the embodiment of the present invention described above, so creating a synergistic effect. Moreover, this is achieved in a structure which is initially thin, and does not substantially alter its thickness, upon absorption, so remaining effective and comfortable.

If the absorbent gelling material is selected among the polyacrylate based polymers described in the European Patent Application EP 05023061.4, referred to above, which are polyacrylate based materials very slightly crosslinked, or substantially not crosslinked at all, the above mentioned synergistic effect can be further improved. The polymers in fact are particularly effective in absorbing complex body fluids such as menses or blood, and upon absorption of such fluids do not generally show a marked swelling, followed by gel blocking, like traditional superabsorbents, but rather act to a certain extent as thickeners of the body fluid, immobilizing it as a sort of gelatinous mass within the absorbent structure, namely in the interstices among the fibers, without causing substantial swelling and in turn a sensible increase of the overall thickness of the absorbent core.

The optional third layer 80 of the absorbent core according to the alternative embodiment of the present invention, which can be provided at the garment facing surface of the absorbent core as illustrated in FIG. 2, can act as an added wicking layer receiving and distributing excess fluid which might not be fully retained by the two upper layers. Again, as explained with reference to the first layer, cellulose fibers and substantial absence of superabsorbent material make the layer particularly effective in acquiring and diffusing the water fraction of body fluids like menses or blood, moreover after at least a part of the complex fraction, particularly the corpuscular components, have been to a certain extent retained by the second layer.

Backsheet

The absorbent article comprising the core according to the present invention can also comprise a backsheet 90. The backsheet primarily has to prevent the extrudes absorbed and contained in the absorbent structure from wetting materials that contact the absorbent article such as underpants, pants, pajamas, undergarments, and shirts or jackets, thereby acting as a barrier to fluid transport. The backsheet according to an embodiment of the present invention can also allow the transfer of at least water vapor, or both water vapor and air through it and thus allow the circulation of air into and water vapor out of the article. The backsheet can typically extend across the whole of the absorbent structure and can extend into and form part or all of side flaps, side wrapping elements or wings, if present.

The various elements of the absorbent article, the topsheet, backsheet and absorbent core according to the present invention can be typically joined to each other according to known techniques to form the absorbent article.

The elements of the article may be joined by any means known in the art for affixing two adjacent layers of material, such that the layers are directly attached to one another or directly attached to one another via the joining means. Suitable joining means include adhesive, fusion bonding, ultra sonic bonding, stitching, heat (e.g. thermo bonding by welding fibers at intersections or melting a polymer to attach fibers or films to each other), embossing, crimping, pressure bonds, dynamic mechanical bonds or combinations thereof.

Especially if the absorbent article finds utility as a sanitary napkin or panty liner, the absorbent article can be also provided with a panty fastening means, which provides means to attach the article to an undergarment. For example the panty fastening means may comprise a panty fastening adhesive on the garment facing surface of the backsheet, or alternatively a mechanical fastener such as hook and loop fasteners such as marketed under the trade name VELCRO, snaps or holders. The panty fastening adhesive provides a means for securing the article to the panty and optionally also a means for securing the article when soiled, to a fold and wrap package for convenient disposal.

The absorbent article comprising the absorbent core of the present invention can be used beneficially in the context of sanitary napkins. The absorbent article may thus also have all those features and parts, which are typical for products in the context of their intended use. For sanitary napkins this includes particularly wings or side flaps which may be provided on the side edges of the napkin and which fold around the crotch edge of an undergarment. The side flaps can be provided as extensions of one or several of the elements of the napkin such as the topsheet and/or backsheet. They can also be made separately and be joined to the side margin of the napkin.

EXAMPLE

An absorbent core according to an embodiment of the present invention comprises a layered structure formed in a continuous process by providing the different layers according to known air laying technique. The structure is calendared and heat treated. The core comprises a first layer comprising 36 g/m$^2$ cellulose pulp fibers and 4 g/m$^2$ bicomponent fibers in a homogeneous mixture, a second layer comprising uniformly mixed 8 g/m$^2$ bicomponent fibers and 32 g/m$^2$ absorbent gelling material particles, and a third layer with the same composition as the first layer. The bicomponent fibers are PET/PE bicomponent fibers available under the trade name Trevira HC255B, 2.2 dtex and 3 mm length, and the absorbent gelling material is available on the market from Nippon Shokubai Co. Ltd. under the trade name Aqualic CA Type QX-L-1074.

The absorbent core has a dry thickness of 1.16 mm and a dry density of 0.103 g/cm$^3$, while wet thickness is 1.44 mm and wet density is 1.05 g/cm$^3$.

Artificial Menstrual Fluid (AMF)

Artificial Menstrual Fluid is based on modified sheep's blood that has been modified to ensure it closely resembles human menstrual fluid in viscosity, electrical conductivity, surface tension and appearance. It is prepared as explained in U.S. Pat. No. 6,417,424, assigned to The Procter & Gamble Company, from line 33 of column 17 to line 45 of column 18, to which reference is made.

The dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "40 mm" is intended to mean "about 40 mm".

All documents cited in the Detailed Description of the Invention are, in relevant part, incorporated herein by reference; the citation of any document is not to be construed as an admission that it is prior art with respect to the present invention. To the extent that any meaning or definition of a term in this document conflicts with any meaning for definition of the same term in a document incorporated by reference, the meaning or definition assigned to that term in this document shall govern.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. An absorbent core for an absorbent article, said core having a wearer facing surface and a garment facing surface, said core comprising a fibrous, layered structure of at least two layers, comprising:
   a first layer having an overall basis weight of from 30 g/square meter to about 60 grams/square meter, the first layer comprising cellulose fibers, synthetic fibers and a latex, wherein the synthetic fibers are present in an amount of between about 7 percent to about 12 percent by weight of the first layer and the latex is present in an amount of less than about 10 percent by weight of the first layer, and wherein the first layer is substantially free of absorbent gelling materials;
   a second layer comprising fibers and an absorbent gelling material, said second layer being substantially free of cellulose fibers, the absorbent gelling material being present in an amount of about 70 percent to about 85 percent by dry weight of the second layer, and wherein said second layer comprises bicomponent synthetic fibers;
   said core comprising less than about 70% cellulose fibers based on the dry weight of said core; and
   said core comprising less than about 70% absorbent gelling materials based on the dry weight of said core, wherein the absorbent gelling materials comprise uncrosslinked polyacrylate.

2. An absorbent core according to claim 1, wherein said core comprises less than about 55% cellulose fibers.

3. An absorbent core according to claim 1, wherein said core comprises from about 10% to about 40% cellulose fibers.

4. An absorbent core according to claim 1, wherein said core comprises from about 10% to about 40% absorbent gelling materials.

5. An absorbent core according to claim 1, wherein said first layer is on said wearer facing surface of said absorbent core.

6. An absorbent core according to claim 1, wherein said core comprises a third layer adjacent to said second layer of said core, said third layer comprising cellulose fibers, and being substantially free of absorbent gelling materials.

7. An absorbent core according to claim 1, wherein said core has a dry density and a wet density, said wet density being from about 5 to about 20 times greater than said dry density.

8. An absorbent core according to claim 7, wherein said dry density is between about 0.04 g/cm$^3$ and about 0.3 g/cm$^3$.

9. An absorbent core according to claim 7, wherein said dry density is between about 0.08 g/cm$^3$ and about 0.15 g/cm$^3$.

10. An absorbent core according to claim 1, wherein said core has a dry density and a wet density, said wet density being from about 8 to about 15 times greater than said dry density.

11. An absorbent core according to claim 1, wherein said absorbent gelling material comprises a polyacrylate based material having an extractable fraction of at least about 30% by weight, evaluated according to the Extractables test method referred to herein.

12. An absorbent core according to claim 1, wherein said absorbent gelling material is a particulate material with an average particle size between about 10µ and about 1,000µ.

13. An absorbent core according to claim 1, wherein said absorbent gelling material is a particulate material with an average particle size between about 50µ and about 1,000µ.

14. An absorbent core according to claim 1, wherein said absorbent gelling material is a particulate material with an average particle size between about 100µ and about 800µ.

15. An absorbent core according to claim 1, wherein said absorbent gelling material is a particulate material with an average particle size between about 150µ and about 600µ.

16. A sanitary napkin comprising an absorbent core according to claim 1.

17. An absorbent core for an absorbent article, said core having a wearer facing surface and a garment facing surface, said core comprising a fibrous, layered structure of at least two layers, comprising:
   a first layer having an overall basis weight of from 30 g/square meter to about 60 grams/square meter, the first layer comprising cellulose fibers, synthetic fibers and a latex, wherein the synthetic fibers are present in an amount of between about 7 percent to about 12 percent by weight of the first layer and the latex is present in an amount of less than about 10 percent by weight of the first layer, and wherein the first layer is substantially free of absorbent gelling materials;
   a second layer comprising fibers and an absorbent gelling material, said second layer being substantially free of cellulose fibers, the absorbent gelling material being present in an amount of about 70 percent to about 85 percent by dry weight of the second layer, and wherein said second layer comprises bicomponent synthetic fibers;
   said core comprising less than about 70% cellulose fibers based on the dry weight of said core; and
   said core comprising less than about 70% absorbent gelling materials based on the dry weight of said core, wherein the absorbent gelling materials comprise uncrosslinked polyacrylate;
   and wherein said core has a dry density and a wet density, wherein said dry density is between about 0.04 g/cm$^3$ and about 0.3 g/cm$^3$.

* * * * *